United States Patent [19]

Rink et al.

[11] Patent Number: 5,269,778
[45] Date of Patent: Dec. 14, 1993

[54] VARIABLE PULSE WIDTH LASER AND METHOD OF USE

[76] Inventors: John L. Rink, 1741-C Mason St., San Francisco, Calif. 94133; Howard S. Cohen, 1105 The Alameda, Berkeley, Calif. 94707

[21] Appl. No.: 765,988

[22] Filed: Sep. 26, 1991

Related U.S. Application Data

[63] Continuation-in-part of Ser. No. 537,138, Aug. 2, 1990, abandoned, which is a continuation of Ser. No. 265,565, Nov. 1, 1988, Pat. No. 4,950,268.

[51] Int. Cl.$^5$ ............................................. A61N 5/06
[52] U.S. Cl. ........................................ 606/12; 606/15
[58] Field of Search ......................................... 606/4-8, 606/10-19

[56] References Cited

U.S. PATENT DOCUMENTS

| | | | |
|---|---|---|---|
| 4,718,417 | 1/1988 | Kittrell et al. | 606/7 |
| 4,939,336 | 7/1990 | Meyer | 606/7 |

FOREIGN PATENT DOCUMENTS

| | | | |
|---|---|---|---|
| 364801 | 4/1990 | European Pat. Off. | 606/4 |
| 8606269 | 11/1986 | World Int. Prop. O. | 606/7 |

*Primary Examiner*—David M. Shay

[57] ABSTRACT

A laser for medical includes an optically pumped laser medium, and the output of the laser is directed through an optical fiber delivery system to a tissue target. The flashlamp is driven by a pulsed power signal that is selectively variable to produce laser pulses of predetermined temporal width and pulse energy, and these values can be selected in accordance with the type of tissue being treated and the tissue effect desired. The laser may be operated to produce relatively brief pulses of high energy, which create a localized plasma at the surface of the target tissue. The plasma effect blocks any significant penetration of the laser beam into the tissue, and each laser pulse causes the ablation of a small portion of the tissue target. Thus thermal necrosis of adjacent and underlying tissue minimized. At the opposite extreme, the laser may be operated to produce relatively long pulses of low or moderate energy, so that the laser beam penetrates the tissue to create such effects as deep coagulation, deep thermal heating and necrosis, and the like. In a further aspect, the laser is provided with an automatic system to control the temporal width of the laser pulses. A photodetector apparatus is optimized to detect the optical radiation from the plasma created at the tissue target and transmitted retrograde through the optical fiber delivery system to the laser. The pulse generating circuitry of the laser terminates the laser pulse in response to the plasma signal. The laser produces tissue effects comparable to a wide range of prior art medical lasers.

7 Claims, 6 Drawing Sheets

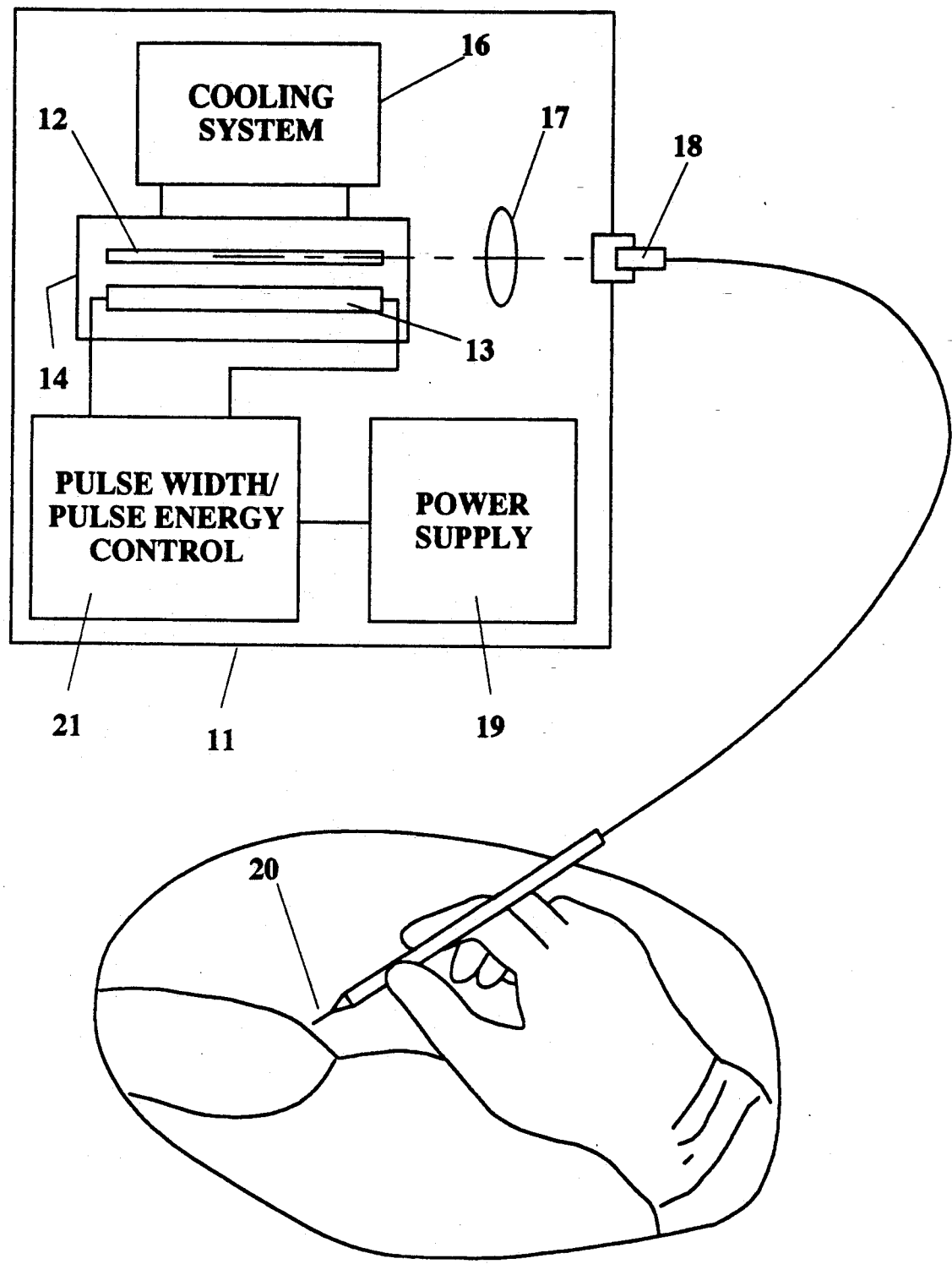
Figure_1

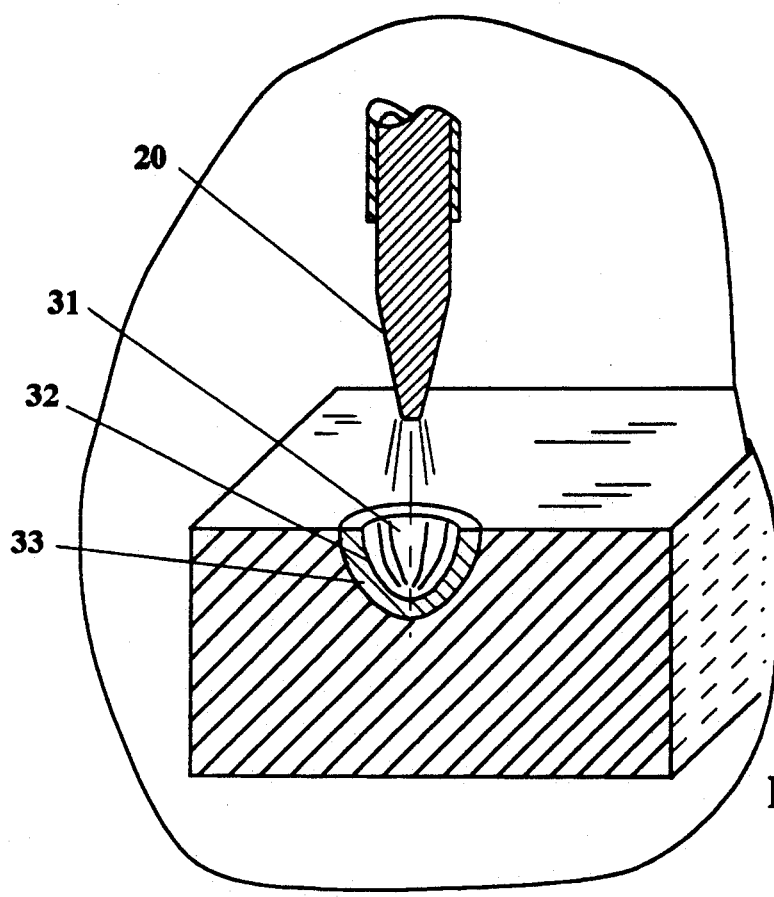
Figure_2
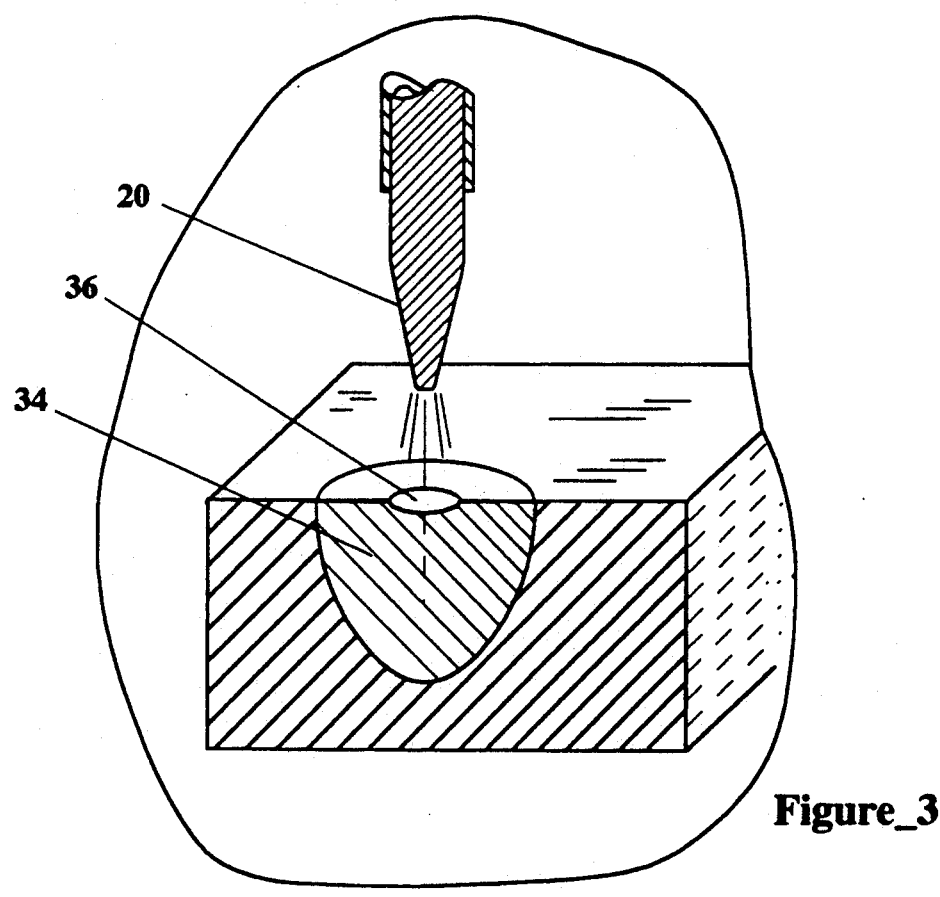
Figure_3

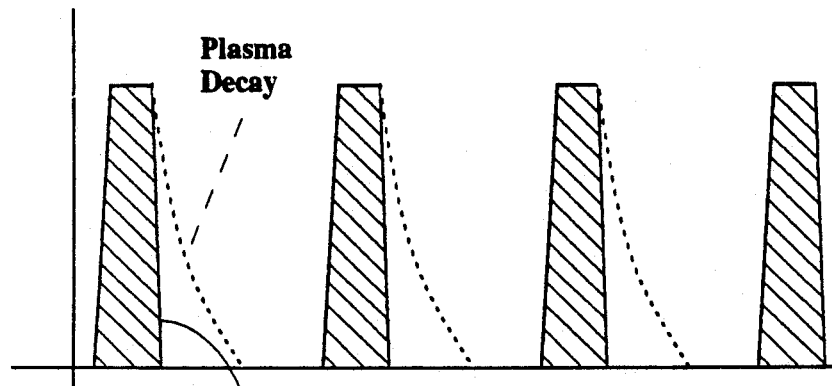
Figure_4a
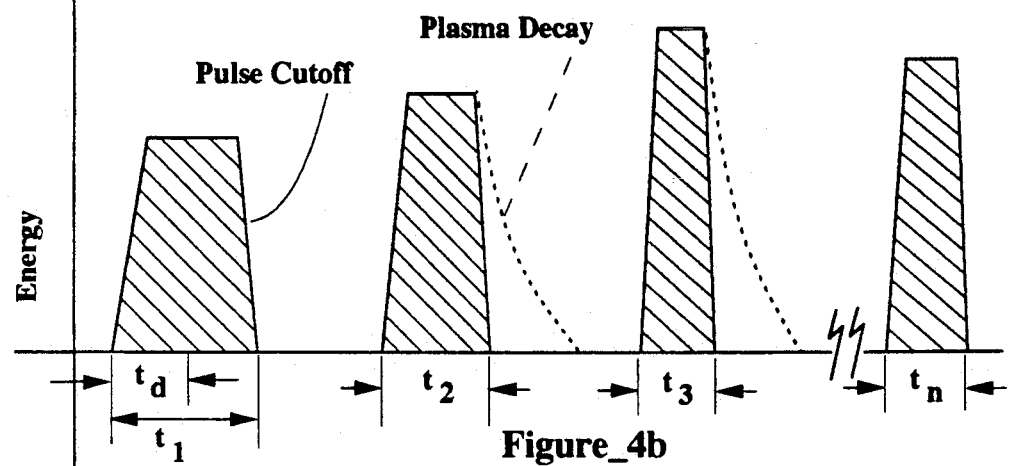
Figure_4b
Figure_4c
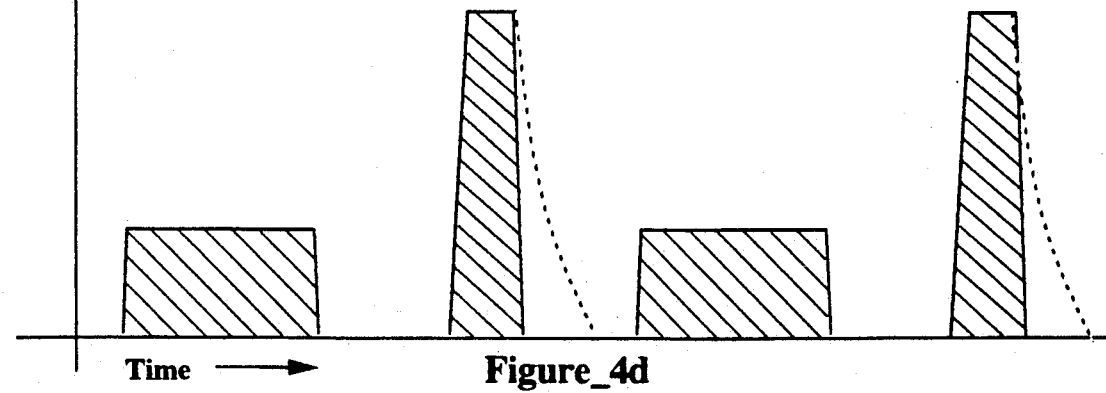
Figure_4d

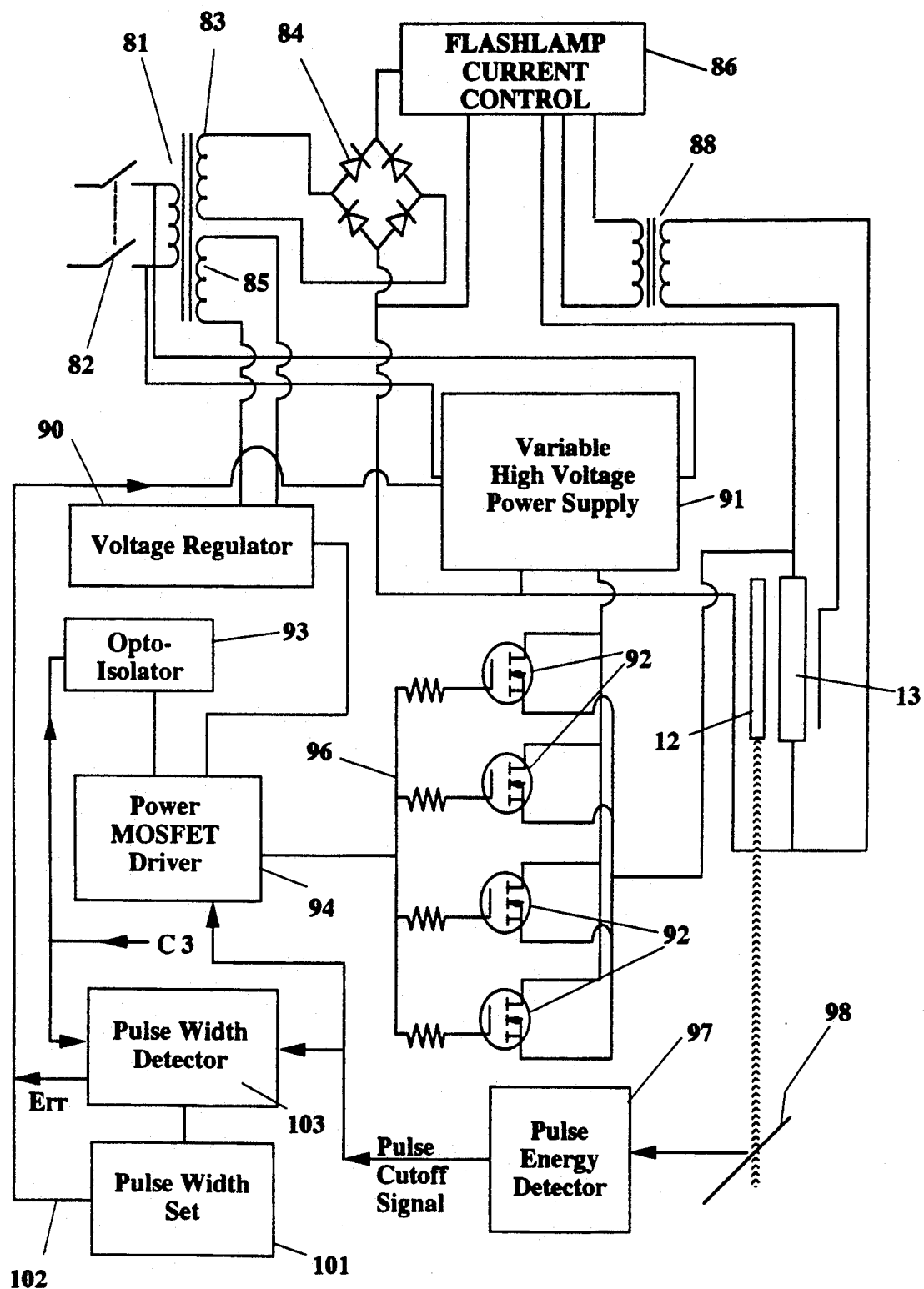
Figure_5

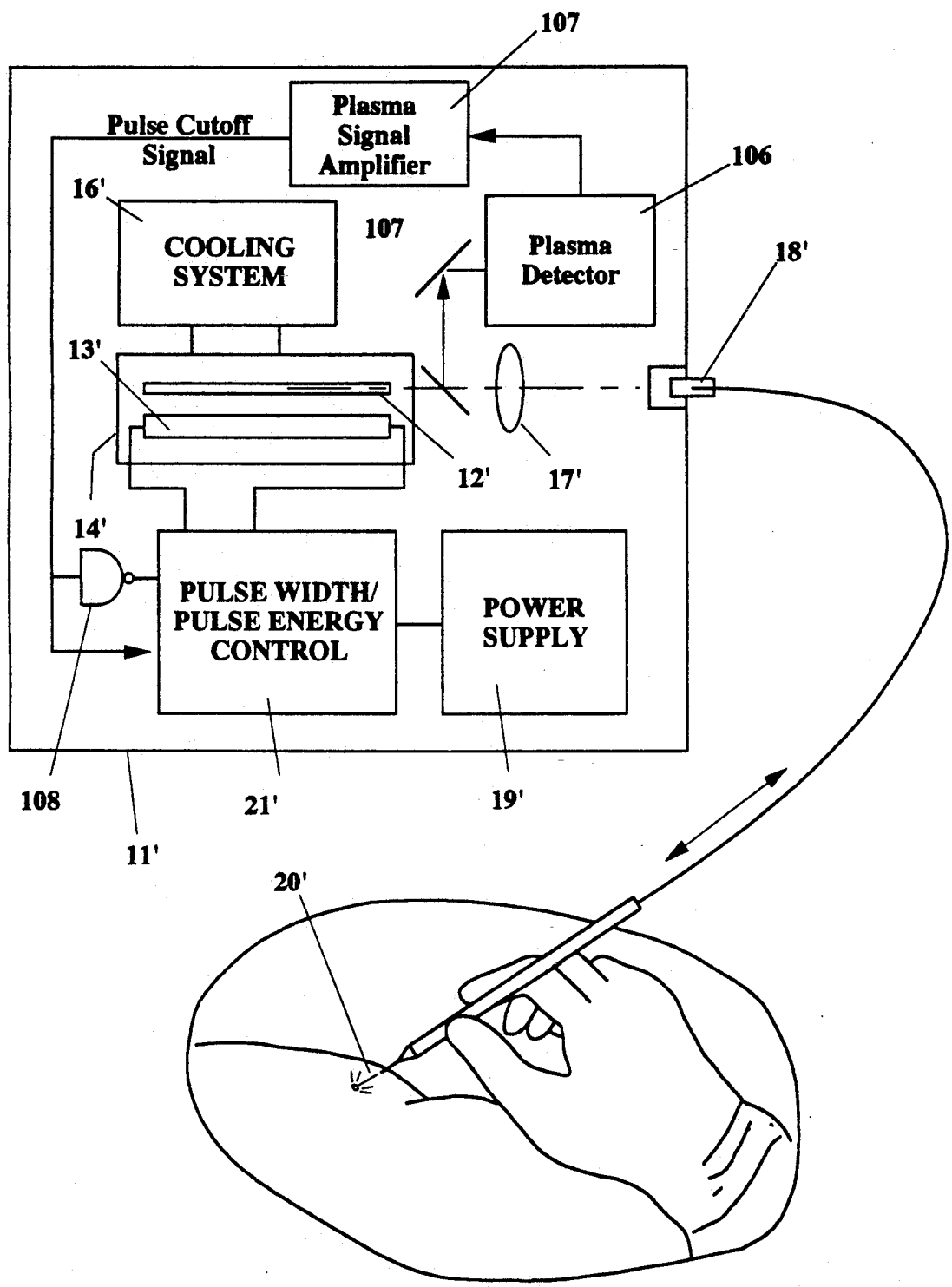
Figure_6

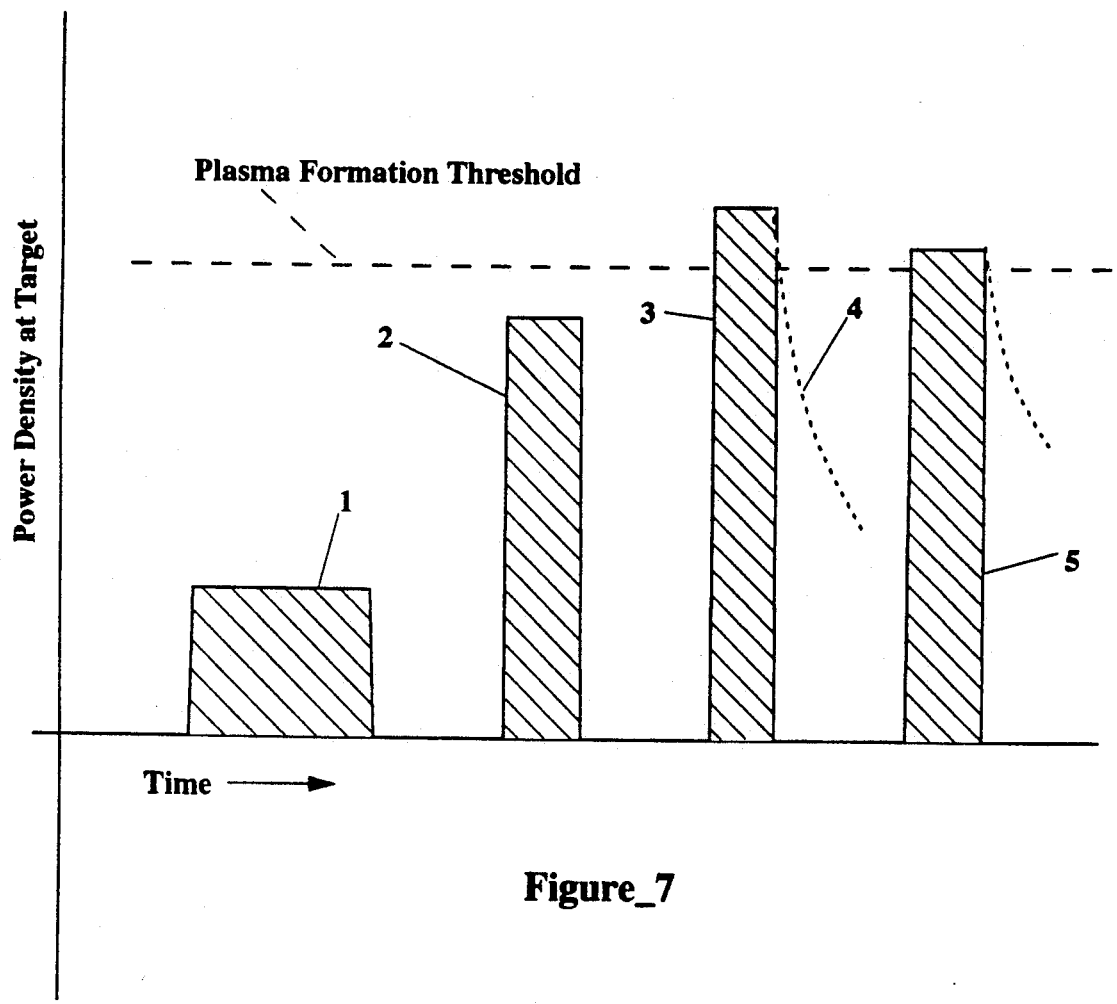
Figure_7

VARIABLE PULSE WIDTH LASER AND METHOD OF USE

REFERENCE TO RELATED APPLICATIONS

This application is a continuation-in-part of application Ser. No. 07/537,138, filed Aug. 2, 1990, now abandoned which is a continuation of application Ser. No. 07/265,565, filed Nov. 01, 1988, now U.S. Pat. No. 4,950,268, issued Aug. 21,1990.

BACKGROUND OF THE INVENTION

The development of lasers for medical use has been driven by the desire to create tissue effects that are beneficial for medical treatment. The tissue effects sought generally comprise cutting, coagulation, hemostasis, and teeth; vascular tissue such as liver and other internal organs, and tumors; fibrous tissue such as muscle and tendon, and non-fibrous tissue such as brain, marrow, and the like.

Medical lasers have been developed on the underlying physical principle that the various constituents of tissue have different absorption characteristics for various wavelengths of light. It follows that a given tissue can be analyzed to determine its primary constituents, the spectral absorption of the constituents can be measured, and a laser having a wavelength that is absorbed in the given tissue can be designed and used for treating the tissue. (This approach presumes a CW or quasi-CW laser output.) For example, water is a primary constituent of many tissue types, and the $CO_2$ laser produces a long infrared wavelength that is absorbed very well in water. As a result, the $CO_2$ laser is very effective in cutting and ablating many tissue types. Likewise, argon lasers and frequency doubled Nd:YAG lasers produce a green wavelength that is well absorbed in hemoglobin, resulting in good surface cutting and hemostasis of bleeding tissue surfaces. On the other hand, Nd:YAG lasers produce a near infrared wavelength that is not well absorbed in water or hemoglobin or other tissue constituents; as a result, the Nd:YAG laser beam penetrates tissue and produces desirable tissue effects such as deep coagulation that other lasers cannot equal.

There are several important disadvantages to the spectral absorption conceptual framework of lasers and tissue effects. First of all, coagulation of tissue is generally desirable not only at the surface of the tissue, but also deep beneath the surface. Laser wavelength that are well absorbed by tissue do not penetrate the tissue and cannot produce deep tissue coagulation, or any other deep tissue effects. As a result, laser light generated by $CO_2$ lasers, Ho:YAG, or frequency doubled Nd:YAG lasers are notably inadequate in tissue coagulation.

Furthermore, due to the fact that each laser wavelength is generally optimized for a particular tissue type and tissue effect, many different lasers are required to carry out the full range of procedures that lasers are capable of performing. Considering that each laser can cost as much as $150,000, it is clear that a medical institution cannot afford to acquire all of the lasers that are necessary. Although some lasers are capable of generating plural wavelengths, these devices still cannot achieve all the tissue effects that are desired. Moreover, multi-wavelength and tunable wavelength lasers are complex, very expensive, and limited in power output.

Thus it is clear that spectral absorption cannot be the primary criterion of laser design for medical use.

It has also been observed in the prior art that pulsed lasers create tissue effects that would not be predicted on the basis of spectral absorption alone. For example, brief laser pulses of relatively high energy can deposit sufficient energy in a small target spot to create a localized crater, regardless of the type of tissue which forms the target and irrespective of the spectral absorption of the laser wavelength by the tissue. This effect is capable of being used as an efficient means of ablating or cutting tissue, and is applicable to virtually any form of tissue. For example, pulsed lasers of relatively low power have been introduced recently for use in dental procedures, and their use in cutting and fusing tooth and bone tissue has been reported.

It has been theorized that pulsed lasers deposit sufficient energy in a brief time at the tissue target to heat the target surface and create a localized plasma. The plasma is generally opaque to light, so that almost all the laser energy is absorbed in the plasma at the surface of the target tissue. The disadvantage of this approach is that the brief pulses of laser energy cannot penetrate to any significant depth in tissue to achieve coagulation, hemostasis, or the like, and this drawback is similar to the drawback noted above; e.g., for $CO_2$ lasers. Also, different tissue types require different instantaneous power densities to generate the plasma effect.

Therefore, despite the advertising claims of manufacturers and the expectations of users, there is no laser available in the prior art that can treat a wide range of tissue types and produce all the tissue effects required to serve all the treatment modalities of modern medical practice.

SUMMARY OF THE PRESENT INVENTION

The present invention generally comprises a novel laser for medical use that is capable of treating a wide range of tissue types and generating virtually all the desired tissue effects required in surgical and medical use. A key feature of the invention is that it produces a pulsed laser output, and both the pulse width and pulse energy are selectable and variable to create almost all desired tissue effects. The invention also comprises the method for use of the laser in medical treatment.

The laser and method of operation and use are also applicable to nonmedical uses, such as industrial or research work with non-physiological substances.

The laser of the present invention includes an optically pumped laser medium, such as a Nd:YAG rod or the like, which is optically coupled to a flashlamp pumping device. Although other laser mediums may be used with the present invention, the Nd:YAG medium is mentioned because it is reliable and rugged, and it produces a primary wavelength (1.064 microns) that is not highly absorbed in any particular tissue type. The output of the laser is directed through an optical fiber delivery system to a tissue target. The flashlamp is controlled by a pulsed power signal that is selectively variable to produce pulses of predetermined temporal width and pulse energy. As a result, the laser generates corresponding laser pulses that are selectively varied in duration and energy, and these values can be selected in accordance with the type of tissue being treated and the tissue effect desired.

For example, the laser may be operated to produce relatively brief pulses of high energy, which will create a localized plasma at the surface of the target tissue. The plasma effect will block any significant penetration of the laser beam into the tissue, and each laser pulse will cause the ablation of a small portion of the tissue target. Thus thermal necrosis of adjacent and underlying tissue is minimized. The pulse width and energy determine an instantaneous power density at the tissue target, and different tissues have different thresholds of instantaneous power density for plasma formation. The variable pulse width and pulse energy that is delivered by the laser permits plasma formation and accelerated cutting and ablation for any tissue type.

At the opposite extreme, the laser may be operated to produce relatively long pulses of low or moderate energy, so that the laser beam falls short of the instantaneous power density required to produce a plasma effect at the target tissue. As a result, the laser beam will penetrate the tissue to create such effects as deep coagulation, deep thermal heating and necrosis, and the like.

The laser of the present invention may generate a series of pulses of the same general temporal width and energy to produce a constant tissue effect, such as surface ablation, or deep coagulation. Alternatively, the laser may be operated to generate different combinations of pulses of varying energy and duration. For example, brief pulses of high energy will produce an optimum tissue ablating effect at the tissue surface, but may not coagulate the resulting bleeding. By interweaving one or more broad, moderate energy pulses among the brief pulses, a coagulation effect can be added to eliminate bleeding as well.

In a further aspect of the invention, the laser is provided with an automatic system to control the temporal width of the laser pulses. The system includes a photodetector apparatus which is optimized to detect the optical radiation from the plasma created at the tissue target. The photodetector apparatus is mounted within the laser and disposed to receive optical energy generated at the target and transmitted retrograde through the optical fiber delivery system to the laser. The photodetector apparatus generates a plasma detection signal upon formation of a plasma at the target. The plasma detection signal is fed to the pulse generating circuitry of the laser, which shuts off the laser pulse in response to the plasma signal. This system assures that no laser energy is wasted in needlessly heating the plasma, and that the maximum tissue effect is achieved for the minimum laser energy incident on the target.

Furthermore, the plasma detection apparatus obviates the need for the user to determine and set the appropriate pulse width to produce the instantaneous power level at the target to generate a plasma. A high energy pulse that is intended to generate a plasma will sustain until the plasma detection signal is received. If the plasma detection signal is not received before the pulse self-terminates, the laser circuit will set a higher energy for the subsequent high energy pulse, and then wait for the plasma detection signal to cut off the pulse. This process is reiterated pulse after pulse until a plasma detection signal is received and the pulse is terminated by the plasma detection signal. In this manner the laser provides automatic optimization of tissue cutting and ablation, and the user does not have to change the laser pulse energy and pulse width settings for changing conditions (e.g., variations in constituents of tissue, variations in distance of the optical fiber operating tip from the tissue, moving the operating tip from one tissue type to another, etc.).

In the lower energy pulse modes, for coagulation, desiccation, and the like, the plasma detection apparatus does not operate to limit the pulse width, due to the fact that a plasma is not generated. Likewise, in operating modes in which high energy, brief pulses are interweaved with relatively longer, lower energy pulses, the plasma detection apparatus does not operate when the longer, lower energy pulses are delivered.

The variable pulse width laser provides laser energy absorption in tissue that is equivalent to the spectral wavelength absorption of wavelength-specific, prior art lasers, while also providing laser beam penetration of tissue for deep tissue effects. Thus the variable pulse width laser can produce almost all the tissue effects of medical and surgical lasers currently available, at a fraction of the cost.

BRIEF DESCRIPTION OF THE DRAWING

FIG. 1 is a functional block diagram of the variable pulse width of the present invention.

FIG. 2 is a diagrammatic depiction of an optical fiber tip delivering laser energy having high instantaneous power density to a target.

FIG. 3 is a diagrammatic depiction of an optical fiber tip delivering laser energy having moderate instantaneous power density to a target.

FIGS. 4a–4d are graphical representations of pulse energy versus pulse width for a variety of pulse outputs of the present invention.

FIG. 5 is a schematic/block diagram of the electronic circuit of the laser of the present invention.

FIG. 6 is a functional block diagram of a further embodiment of the invention, showing a laser system including a plasma detection apparatus.

FIG. 7 is a graphical representation of power density versus time for a series of pulses generated by the embodiment of the laser depicted in FIG. 6.

DESCRIPTION OF THE PREFERRED EMBODIMENT

The present invention generally comprises a laser for medical use that is capable of treating a wide range of tissue types and generating virtually all the desired tissue effects required in surgical and medical use. A key feature of the invention is that it produces a pulsed laser output, and both the pulse width and pulse energy are selectable and variable to create many different desired tissue effects. The invention also comprises the method for use of the laser in medical treatment.

With regard to FIG. 1, one embodiment of the invention includes a laser 11 which includes a lasing medium 12 and an optically pumping flashlamp 13. The lasing medium may preferably comprise a Nd:YAG crystal rod, as is known in the prior art, or any equivalent material. The Nd:YAG produces a primary output at a wavelength of 1.06 micron, and is preferred due to the fact that this wavelength is not highly absorbed by any type of tissue, and is therefor capable of penetrating most tissue and physiological structures. The lasing medium 12 and flashlamp are enclosed in a laser cavity 14, as is known in the prior art, and a cooling system 16 is connected to the cavity to remove excess heat therefrom.

The laser beam output is coupled by a lens 17 to the input end 18 of an optical fiber delivery system. At the distal output end 20 of the optical fiber, the laser energy is directed to perform useful work in a surgical/medical procedure.

The laser 11 includes a power supply 19 which feeds a pulse control system 21. The pulse control system provides electrical pulses of varying duration and pulse energy, and is connected to feed the electrical pulses to the flashlamp 13. The flashlamp is driven by the electrical pulses to emit corresponding light pulses, resulting in laser pulses which correspond in energy and duration to the electrical pulses. Thus the laser is operated to generate a pulsed output which is controlled and selectively variable in both pulse energy and pulse duration.

It is known in the prior art that brief, high energy pulses of laser light, when directed at a target tissue, may have sufficient instantaneous power density to vaporize and form a plasma at the target surface. Such pulses are depicted in FIG. 4a. As shown in FIG. 2, when a plasma 31 forms at the target surface, a crater 32 is excavated into the surface. Also, the presence of the plasma, which is opaque to light, blocks the passage of the laser beam to the target tissue and limits the zone 33 of thermal tissue damage to a relatively thin portion surrounding the crater 32. Repeated pulses directed at the same spot, if they are sufficiently spaced to allow the plasma of the previous pulse to decay, will further the excavation and lead to the formation of a tissue ablation effect that progresses rapidly. If the optical fiber tip 20 is moved along the surface of the target, the result is a line of severance extending into the target surface. Repeated passes will deepen and/or widen the line to form an incision. These effects are obtained whether or not the tip 20 is in contact with the target tissue.

The minimum instantaneous power density at the target surface required to ignite a plasma differs for different tissue types, based on their varying constituents (water and mineral content, density, etc.). Thus, by varying the pulse energy and pulse duration of the laser output, virtually any type of tissue, from bone and teeth to tendon to liver and spleen can be incised and/or ablated without sustaining any significant collateral tissue damage.

On the other hand, the laser may be operated to generate pulses of longer duration and less peak power, as depicted in FIG. 4c. In this case a plasma is not formed at the target spot 36, and, as shown in FIG. 3, there is very little ablation at the target spot. Rather, the laser energy penetrates the surface far more effectively, causing a zone 34 of tissue irradiation at a depth far greater than the brief laser pulses. The deep tissue irradiation produces such effects as deep tissue coagulation, dessication, and photodynamic destruction of some forms of tissue (e.g., photosensitive or photosensitized tumors). The fiber tip 20 may be spaced apart from or in contact with the target tissue. In the broad pulse mode, the operating tip 20 may be used to cut tissue in direct contact with the tissue, due to the fact that the laser energy heats the tip sufficiently so that it thermally destroys the tissue in contact therewith.

As shown in FIG. 4d, the pulse width/pulse energy control system may be operated to provide interleaved pulses of differing duration and energy. For example, brief, high energy pulses may be alternated with longer, less energetic pulses. The brief pulses provide optimum tissue cutting, while the broad pulses produce a coagulation effect that is desirable when cutting vascular tissue. Likewise, a series of broad pulses used for deep coagulation may be interrupted by one or more brief, energetic pulses which serve the purpose of removing smoke, carbonization, and other contaminants from the operating tip 20. Various combinations of pulses may be employed to achieve a wide variety of tissue effects and to optimize the useful work produced by the laser energy.

For purposes of discussion in this specification, narrow pulses are generally within the range of 10–500 microseconds, and broad pulses are generally within the range of 500–2000 microseconds.

The laser system depicted in FIG. 1 may be carried out using the circuit of FIG. 5, which is a modified form of the circuit described in parent patent U.S. Pat. No. 4,950,268, issued Aug. 21, 1990. The circuit includes a transformer 81 connected through a main shutoff relay switch 82 to 110 (or 220) VAC utility power. The transformer 81 includes a high voltage secondary winding 83 having an output of approximately 600 volts that is connected across a full wave bridge rectifier 84. The rectified voltage is fed to a flashlamp current control circuit 86, which includes filter capacitors that produce a smooth DC current that in turn is connected to one electrode of a flashlamp 13. The other electrode of the flashlamp is connected to one output terminal of the rectifier 84. The circuit 86 applies approximately 160 VDC to the flashlamp 13 to maintain the lamp plasma in a conductive state, emitting light at a level well below the threshold of lasing in the Nd:YAG rod. The current control circuit is also connected to a spark transformer 88, which has a high voltage output connected to a spark electrode 89 adjacent to the flashlamp 13. The spark transformer is activated by circuit 86 to provide a high voltage pulse to initiate flashlamp conduction, after which the circuit 86 provides a steady "simmer" current to maintain conduction in anticipation of a high current pulse to dramatically increase flashlamp output and initiate lasing.

To provide the high current pulse, the driver circuit includes a variable high voltage power supply 91 connected across the utility power supply. One output terminal of the power supply 91 is connected to one electrode of the flashlamp, and the other output is connected to the drain terminals of a plurality of power MOSFETs 92 in a parallel configuration. The source connections of the MOSFETs 92 are connected in parallel fashion to the other flashlamp electrode. Thus switching of the MOSFET devices causes the output of the power supply 91 to be applied directly across the flashlamp, and this branch of the circuit provides the substantial current required to sustain the output of the flashlamp at levels necessary to cause lasing.

Switching of the MOSFETs 92 is accomplished by signal $C_3$, which is fed to an opto-isolator 93 which isolates the logic circuits from the power circuits. The output of the isolator 93 is conducted to a power MOSFET driver circuit 94 connected in series with a parallel array of MOSFET gates 96. This arrangement provides a high current source required to overcome the intrinsic gate-to-channel capacitance and switch the MOSFETs 92 as rapidly as possible. Thus whenever signal $C_3$ goes high, the MOSFETs 92 are switched on to provide high current to the flashlamp to sustain the lamp output as long as $C_3$ remains high. As soon as $C_3$ drops to zero, the MOSFETs switch off, lamp output ceases, and the maintenance voltage increases once again.

The power MOSFET driver 94 is energized by a secondary winding 85 of the transformer 81, which is connected to a voltage regulator 90. The regulated output of the voltage regulator 90 is connected to the power MOSFET driver 94.

The circuit also includes a pulse energy detector 97 which is positioned to receive a small portion of the output of the laser medium 12. The detector may be disposed in axial alignment with the rear mirror of the laser cavity, or a partial mirror 98 may reflect a small portion of the laser beam to the detector, as is known in the prior art. The pulse energy detector monitors each laser pulse in real time, and generates a pulse cutoff signal when each laser pulse attains a preset energy level. The preset energy level may be fixed or adjustable. The pulse cutoff signal is conducted to the power MOSFET driver 94 to turn off the MOSFETs 92 and terminate each pulse when the preset pulse energy is attained.

A pulse width set device 101, which may comprise a manual or an automatic device, is connected through line 102 to the variable high voltage power supply 91. The pulse width set device provides a default control signal to the power supply 91 which causes the power supply 91 to vary its voltage output to the power MOSFETS 92 and thus to the flashlamp 13. The voltage determines the intensity of the optical pumping effect, and controls the peak energy of the corresponding laser pulse. However, the pulse energy detector 97 will terminate the pulse when the preset pulse energy is reached, and the pulse may not attain the desired duration of the pulse width set device 101.

The invention also provides a pulse width detector 103 which receives the pulse width set value of the device 101, as well as the pulse start signal $C_3$ and the pulse cutoff signal from the pulse energy detector 97. The detector 103 determines the duration of each pulse as it is terminated, and compares the duration with the set value of the device 101. The output of the pulse width detector 103 is an error signal on line 102 that serves to alter the voltage output of the variable high voltage power supply from the default setting provided by the pulse width set device 101.

The operation of the pulse width/pulse energy portion of the circuit may be described as follows. A desired pulse width is entered in the pulse width set device 101, which generates a corresponding default control signal on line 102 to variable high voltage power supply 91. The power supply 91 sets a voltage output in response to the control signal on line 102. When signal $C_3$ goes high, the power MOSFETS conduct the voltage from the power supply 91 through the flashlamp 13 to generate a laser pulse having a peak energy which corresponds to the voltage from the power supply 91. The pulse energy detector 97 monitors the pulse, and generates a pulse cutoff signal when a preset pulse energy is reached.

For example, with reference to FIG. 4b, the first pulse may have a duration $t_1$, which is greater than the desired duration $t_d$. This duration is required to deliver all the laser energy required to cause the pulse energy detector to generate the pulse cutoff signal. The pulse width detector 103 evaluates the actual pulse width with respect to the preset pulse width from device 101, and the resulting error signal is fed to the power supply 91 for the next pulse. The next pulse has a higher peak energy, due to an increase in the voltage from the power supply 91 to the flashlamp, and a duration $t_2$ which is still greater than the desired duration $t_d$. As before, the second pulse is terminated by the pulse energy detector 97, so that the first and second pulses have equal energies (and the graphical representations have equal areas in FIG. 4b). The error signal from pulse width detector 103 after the second pulse further increases the voltage from power supply 91, and the third pulse is cutoff at a duration $t_3$ that is approximately equal to the desired duration $t_d$. This process is reiterated as long as the laser remains in operation, and it is significant to note that the variable, preset pulse width is attained without deviating from the predetermined pulse energy value.

It should be noted that the circuit of FIG. 5 can deliver pulse sequences of interleaved broad and narrow pulses, as described previously and depicted FIG. 4d, by automatically changing the setting of the pulse width set device 101 as the pulse train output continues.

As noted previously, the formation of a plasma by the laser pulses at the tissue target is often desirable for cutting and ablating many types of tissue. Plasma formation may be achieved by manually setting the pulse energy and pulse duration to values which are known by empirical data to produce plasma formation for the particular type of tissue being treated. The invention also provides an automatic system for achieving the same result. With regard to FIG. 6, a further embodiment of the invention is described in which components similar to components of the embodiment of FIG. 1 are given the same reference numerals with a prime (') designation. The laser 11' includes components 12'-14', and 16'-21' that correspond in description and function to FIG. 1.

The embodiment of FIG. 6 includes a plasma detector 106 with in the laser 11', comprising a photodetector that is adapted to detect the light emissions from a plasma created by a laser pulse. It is known that a plasma is a superheated gas that emits a strong optical signal. A portion of that plasma optical signal is picked up by the operating tip 20't0 of the optical fiber delivery system, and transmitted retrograde through the optical fiber. A mirror arrangement 107 is disposed to direct retrograde light from the input end of the optical fiber to the plasma detector. The mirror arrangement may include selectively reflective surfaces that do not reflect the laser wavelength, and may include other filtering means to block laser light from reaching the plasma detector 106. The plasma detector generates a signal that commences with the formation of a plasma by a laser pulse at the target surface. The plasma detector signal is amplified and buffered by plasma signal amplifier 107 to form a pulse cutoff signal which is fed to the pulse width/pulse energy control 21'.

The plasma cutoff signal is used to provide two functions for the pulse width/pulse energy control 21'. When a plasma is ignited at the target site, with the operating tip either in free beam or contact mode, the plasma signal will cause the laser to immediately terminate the laser pulse that formed the plasma. This function assures that the maximum tissue ablation or cutting is achieved at the target, while preventing unnecessary and wasteful lasing after the plasma is created. (The plasma is generally opaque to light energy, and further laser energy directed at the target site will be blocked from reaching the target and will only needlessly heat the plasma.)

Furthermore, if a pulse is terminated by the pulse energy detector 97 of FIG. 5 without causing plasma formation, the absence of a signal from the plasma detector indicates that the pulse had insufficient instantaneous power density at the target site to create a plasma. Thus, the pulse cutoff signal from the plasma detector may be fed through a NAND gate 108 to a portion of the pulse width/pulse energy control 21' to increase the instantaneous pulse energy of the subsequent laser pulse. For example, NAND gate 108 may lead to the error signal line 102 of FIG. 5 to introduce a correction signal which increases the voltage to drive the subsequent laser pulse.

Thus, the plasma detector apparatus is used to drive the pulse width control to seek the formation of a plasma. As shown in FIG. 7, the first pulse 1 from the laser may have insufficient power density to reach the plasma formation threshold of the target material. The absence of a plasma will cause the control circuitry to increase the peak energy of the next laser pulse, so that pulse 2 will increase in power density at the target site. Pulse 3 is greater still in power density, and exceeds the plasma threshold. The plasma decay 4 is very rapid after pulse cutoff. Pulse 5 is lower in power density, but still exceeds the threshold of plasma formation. The circuity will maintain the pulse energy at the preset level, while seeking the appropriate pulse duration to ignite a plasma. Once the pulse cutoff signal from the plasma detector is received by the control 21', the pulse is terminated immediately and the pulse peak energy is no longer increased.

It should be noted that the method of the present invention involves the use of laser pulses of varying width and energy to achieve predetermined tissue effects, and includes all of the functions and combinations of pulse parameters described above. It also includes the method of controlling a laser output using a plasma detection signal from the laser target. Furthermore, it should be noted that the invention is not limited to use with Nd:YAG lasers, but may be applied to a wide variety of laser mediums and laser power supplies.

We claim:

1. A laser operating system, including;
a laser medium,
means for operating said laser medium in a pulse mode to generate a plurality of laser output pulses in a temporal sequence, each pulse having a temporal duration and energy
a delivery system for transmitting the laser output to a target,
means for selectively varying the temporal duration and energy of each of said plurality of pulses to produce a predetermined instantaneous power density at the target,
means for increasing said instantaneous power density of successive pulses of said plurality of pulses,
means for detecting plasma formation at the target and generating a plasma signal, and
means for defeating said means for increasing said instantaneous power density in response to said plasma signal.

2. The laser operating system of claim 1, further including means for terminating each of said plurality of laser output pulses in response to said plasma signal.

3. The laser operating system of claim 1, wherein said delivery system is disposed to transmit radiant energy from said target retrograde to said laser, and said means for detecting the formation of a plasma at the target and generating a plasma signal includes photodetector means for monitoring retrograde light transmission from said delivery system.

4. The laser operating system of claim 3, wherein said photodetector means includes a photosensor, and filter means for blocking laser generated light from said photosensor.

5. A method for laser surgery, comprising the steps of;
providing a laser having an output coupled to a delivery system directed at a tissue target,
operating the laser to produce a plurality of pulses in a temporal sequence, each pulse having a temporal duration and energy,
selectively varying the temporal duration and energy of each of said plurality of pulses to produce a predetermined instantaneous power density at the tissue target,
receiving radiant emissions including light transmitted retrograde in said delivery system from said target tissue and detecting a plasma emission portion of said radiant emissions emitted by plasma formed at the target tissue, and
terminating each pulse of said temporal sequence upon detection of said plasma emission.

6. The method of claim 5, further including the step of monitoring the light transmitted retrograde in said delivery system to detect the radiant emissions from the tissue target.

7. The method of claim 5, further including the step of increasing said instantaneous power density of successive pulses in said temporal sequence, and ceasing the increase of instantaneous power density of successive pulses upon detection of said plasma emission.

* * * * *